US00PP33103P3

(12) United States Plant Patent

Klemm et al.

(10) Patent No.: US PP33,103 P3

(45) Date of Patent: May 25, 2021

(54) *CALIBRACHOA* PLANT NAMED 'KLECA18483'

(50) Latin Name: ***Calibrachoa* sp.**
Varietal Denomination: KLECA18483

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/871,008

(22) Filed: May 10, 2020

(65) Prior Publication Data

US 2020/0383256 P1 Dec. 3, 2020

Related U.S. Application Data

(60) Provisional application No. 62/921,069, filed on May 29, 2019.

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ... A01H 5/02; A01H 5/12; A01H 5/00; A01H 6/82; A01H 6/821; A01H 6/14
See application file for complete search history.

(56) References Cited

PUBLICATIONS

Mast Young Plants 2018/2019, retrieved on Oct. 15, 2020, retrieved from the Internet at http://www.mastyoungplants.com/wp-content/uploads/2018/10/MYP-2018_2019-Catalog.pdf, 3 introductory pages, pp. 2-7, 29, 144. (Year: 2019).*

Selecta One 2021, retrieved on Oct. 15, 2020, retrieved from the Internet at https://www.ballseed.com/Pdf/catalogs/Selecta_2021_Catalog_2091778.pdf, 3 introductory pages, pp. 2,118. (Year: 2020).*

* cited by examiner

*Primary Examiner* — June Hwu
(74) *Attorney, Agent, or Firm* — Weatherly IP Solutions, LLC; Barbara Campbell

(57) ABSTRACT

A new *Calibrachoa* plant designated 'KLECA18483' particularly distinguished by light pink flowers, is disclosed.

1 Drawing Sheet

Genus and species: *Calibrachoa* sp.
Variety denomination: 'KLECA18483'.

BACKGROUND OF THE NEW PLANT

The present invention comprises a new and distinct variety of *Calibrachoa*, botanically known as *Calibrachoa* sp., and hereinafter referred to by the variety name 'KLECA18483'. 'KLECA18483' originated from a controlled cross between the proprietary female *Calibrachoa* parent 'KLECA12235' (U.S. Plant Pat. No. 25,287) also designated 'CA-2009-1427' and known commercially as MINIFAMOUS Neo 'White' and the proprietary male *Calibrachoa* 'CA-2014-4088', (unpatented) in Stuttgart, Germany in August 2015.

'KLECA18483' has been found to reproduce true to type in successive generations of asexual propagation in Stuttgart, Germany via vegetative stem cuttings.

SUMMARY

The following are the most outstanding and distinguishing characteristics of 'KLECA18483' when grown under normal horticultural practices in Stuttgart, Germany.

1. Pink flowers; and
1. An upright, mounding habit.

DESCRIPTION OF THE PHOTOGRAPH

This new *Calibrachoa* plant is illustrated by the accompanying photograph of a plant grown outdoors in Stuttgart, Germany. The photograph shows the whole plant, unless otherwise noted, including the flowers and foliage and buds. The colors shown are as true as can be reasonably obtained by conventional photographic procedures. The photograph is of a whole plant photo of 'KLECA18483', 4-months old, taken in June 2018.

DESCRIPTION OF THE NEW VARIETY

The following detailed descriptions set forth the distinctive characteristics of 'KLECA18483'. The data which define these characteristics were collected from asexual reproductions carried out in Stuttgart, Germany. Data was collected on plants grown 18 weeks since potting in a greenhouse with no pinching or growth regulators. Color references are to The R.H.S. Colour Chart of The Royal Horticultural Society of London (R.H.S.), 5$^{th}$ edition (2007).

Classification:

*Family*.—Solanaceae.
*Botanical*.—*Calibrachoa* sp.
*Designation*.—'KLECA18483'.

Parentage:
*Female parent*.—'KLECA12235' (U.S. Plant Pat. No. 25,287).
*Male parent*.—'CA-2014-4088' (unpatented).
Plant:
*Life cycle*.—Annual.
*Form*.—Short-lived subshrub.
*Habit*.—Upright, mounding.
*Height* (*from soil line to top of foliage*).—22 cm.
*Spread*.—46 cm.
*Propagation*.—Vegetative.
*Type cuttings*.—Tip cuttings.
*Time to produce a rooted cutting*.—3 weeks.
*Disease and pest resistance/susceptibility*.—To date, plants of 'KLECA18483' have not been observed to be resistant or susceptible to pathogens and pests common to *Calibrachoa* plants.
Stems:
*Stem color*.—RHS 143C.
*Pubescence*.—Present.
*Pubescence color*.—RHS 155A.
*Stem diameter*.—0.2 cm.
*Stem length*.—From soil line to first node: 1.8 cm. Total length: 38 cm.
*Internode length*.—1.2 cm.
Foliage:
*Arrangement*.—Opposite.
*Shape*.—Lanceolate.
*Apex*.—Broadly acute.
*Base*.—Attenuate.
*Margin*.—Entire.
*Surface*.—Moderately glandular pubescent.
*Surface pubescence*.—Present.
*Pubescence color*.—RHS 155A.
*Venation*.—Arcuate.
*Venation color*.—Upper surface: RHS 144A. Lower surface: RHS 145B.
*Length*.—3.6 cm.
*Width*.—1.0 cm.
*Color*.—Upper surface: RHS 137A. Lower surface: RHS 137D.
*Fragrance*.—Absent.
Inflorescence:
*Flowering habit*.—Single flowers.
*Flower type*.—Determinate inflorescence.
*Flowering requirements*.—A minimum of light sun is required.
*Duration of flowers*.—6 days.
*Shape*.—Funnel form.
*Lobing of the flower*.—Medium.
*Conspicuousness of the veins of the flower*.—Very weak for the upper surface and weak for the inner surface.
*Fragrance*.—Absent.
*Flower depth*.—2.8 cm.
*Flower tube length*.—2.1 cm.
*Flower tube diameter*.—0.6 cm.
*Flower diameter*.—4.0 cm.
*Calyx*.—Funnel shaped, salverform.
Inflorescence bud:
*Surface*.—Smooth.
*Length*.—2.7 cm.
*Diameter*.—0.5 cm.
*Shape*.—Oblong.
*Color*.—RHS 77B (limbs) and RHS 150D (throat).
Peduncles:
*Length*.—2.2 cm to 3.0 cm.
*Diameter*.—0.1 cm.
*Color*.—RHS 144B.
*Texture*.—Densely glandular pubescent.
*Anthocyanin color*.—Absent.
Sepals:
*Shape*.—Lanceolate.
*Apex*.—Narrowly acute.
*Margin*.—Entire.
*Length*.—1.6 cm.
*Diameter*.—0.35 cm.
*Sepal color*.—Upper surface: RHS 137A. Lower surface: RHS 137C.
Petals:
*Shape*.—Obcordate.
*Length*.—2.0 cm.
*Apex*.—Emarginate.
*Margin*.—Entire.
*Base*.—Fused in the tube.
*Texture, upper surface*.—Glabrous.
*Texture, lower surface*.—Glandular pubescent, dense along venation.
*Lobe length*.—2.0 cm.
*Lobe width*.—1.7 cm.
*Color*.—Lobe color: Upper surface: Close to RHS N74A but more shiny. Lower surface: RHS N74C. Corolla tube color: Inner: RHS 8B with a very small transition area of RHS NN155C. Outer: RHS 8D. Corolla transition area: Very small. Immature and fading color: Not different than mature color.
*Fragrance*.—Absent.
Reproductive organs:
*Stamen number*.—5.
*Anther color*.—RHS 13A.
*Filament color*.—RHS 1C.
*Pollen color*.—RHS 8B.
*Placenta arrangement*.—Ovate.
*Pistil number*.—1.
*Pistil length*.—1.2 cm.
*Stigma color*.—RHS 143A.
*Style length*.—1.0 cm.
*Style color*.—RHS 149C.
Fruit and seed set: No fruit or seed set observed.

COMPARISON OF 'KLECA18483' WITH PARENTAL LINES AND KNOWN VARIETY

'KLECA18483' is distinguished from the parental lines as follows. Whereas 'KLECA18483' has a main lobe color of close to RHS N74A but more shiny, the female parent 'KLECA12235' and male parent 'CA-2014-4088' have main lobe colors of RHS NN155D.

'KLECA18483' can be compared to the commercial *Calibrachoa* variety 'Unique Hot Pink' (patent status unknown) as follows. 'KLECA18483' has an upright, mounding habit and no color transition to corolla tube, whereas 'Unique Hot Pink' has a semi-trailing habit and a medium area of main color transition to corolla tube. Additionally, 'KLECA18483' has less vigor than 'Unique Hot Pink'.

We claim:

1. A new and distinct variety of *Calibrachoa* plant designated 'KLECA18483' as illustrated and described herein.

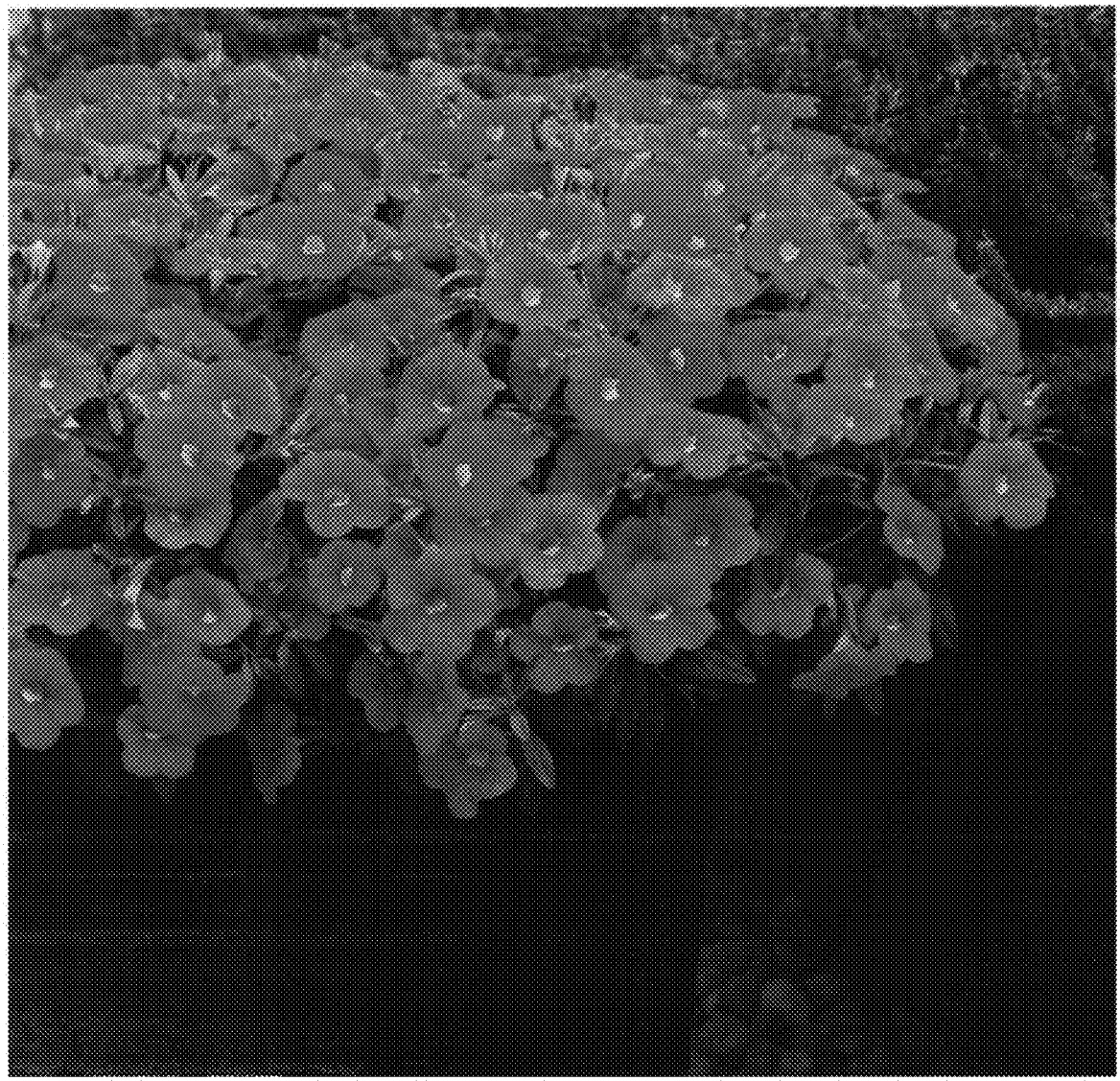

* * * * *